United States Patent [19]

Kaneko et al.

[11] Patent Number: 4,588,818
[45] Date of Patent: May 13, 1986

[54] METHOD FOR RECOVERY OF OPTICALLY ACTIVE TRYPTOPHANE

[75] Inventors: Tetsuya Kaneko, Kawasaki; Toshio Kitahara, Yokosuka; Toyokazu Kaneko, Sagamihara, all of Japan

[73] Assignee: Ajinomoto Co., Inc., Tokyo, Japan

[21] Appl. No.: 668,940

[22] Filed: Nov. 7, 1984

[30] Foreign Application Priority Data

Nov. 10, 1983 [JP] Japan .................... 58-211593

[51] Int. Cl.$^4$ .......................................... C07D 209/20
[52] U.S. Cl. ............................................... 548/498
[58] Field of Search ...................................... 548/498

[56] References Cited

U.S. PATENT DOCUMENTS 3,129,122 9/1964 Sacoji et al. ............... 548/498 X
3,825,559 7/1974 Tazuke et al. .................. 548/498

FOREIGN PATENT DOCUMENTS 2145394 3/1972 Fed. Rep. of Germany ...... 548/498
1302248 7/1962 France ................................. 548/498
58-000895 6/1983 Japan .

Primary Examiner—Richard L. Raymond
Assistant Examiner—D. B. Springer
Attorney, Agent, or Firm—Oblon, Fisher, Spivak, McClelland & Maier

[57] ABSTRACT

A method for recovery of optically active tryptophane, which comprises filtering a solution of optically active tryptophane containing impurities through a semipermeable membrane; adding a lower alcohol or a ketone to the filtrate; maintaining the solution containing the lower alcohol or ketone at an alkaline pH and a temperature higher than the $\alpha/\beta$ crystalline transition point; adding acid to the solution, thereby causing crystals of optically active tryptophane to form in the solution; and separating the crystals from the solution containing impurities, is disclosed. This method avoids the use of resins in the purification steps.

10 Claims, No Drawings

METHOD FOR RECOVERY OF OPTICALLY ACTIVE TRYPTOPHANE

DETAILED DESCRIPTION OF THE INVENTION

The present invention relates to a method for recovery of optically active tryptophane comprising a treatment of a solution of optically active tryptophane containing impurities, namely, a fermentation liquid or an enzyme reaction mixture and liquids obtained at intermediate steps thereof, with a semi-permeable membrane and recrystallization in combination, for the purpose of removing the concomitant impurities contained therein to perform purification more effectively.

L-Tryptophane is one of the essential amino acids and useful as a nutrient source of human and domestic animals. It is thus desired that L-tryptophane to be so used be of high quality.

To produce tryptophane, a chemical synthesis method, a fermentation method, an enzyme method and the like have been performed. The chemical synthesis method requires optical resolution of a racemic form. In the fermentation method and the enzyme method, optically active tryptophane can be produced directly but broth obtained thereby contains large quantities of concomitants and pigments so that steps and operations for recovering tryptophane therefrom are extremely complicated.

Heretofore, as methods for removing these concomitant impurities, there are known, for example, a method which comprises adsorbing tryptophane on an anion exchange resin, eluting it, further adsorbing tryptophane to a cationic ion exchange resin, eluting it, and then crystallizing it (Japanese Published Unexamined Patent Application 11061/78) and a method which comprises contacting a solution of tryptophane crude crystals with a non-ionic resin to adsorb impurities thereto, then performing a filtration treatment using an ultrafiltration membrane, and then performing crystallization (Japanese Published Unexamined patent Application 895/83).

However, tryptophane shows strong molecular adsorption to resins due to a peculiar affinity resulting from its molecular structure. Accordingly, tryptophane has a tendency to adsorb and desorb to resins together with impurities such as coloring materials. In order to separate these impurities, steps and operations using resins become complicated or are accompanied by serious losses such as loss of residue after elution. In addition, large quantities of water, acids, alkalis, organic solvents, etc., are employed in steps for using resins so that costs for side raw materials, treatment of waste liquid, and energy increase. Further, optically active tryptophane tends to cause distortion in its crystal form due to adsorption of impurities, such as color formation, and also tends to form aggregated crystals, thereby including a large amount of impurities in the intervals of the crystals. For these reasons, no method for obtaining optically active tryptophane in high yield and high quality without using resins is known.

As a result of investigations directed toward a process for recovering optically active tryptophane excludes any step of using resins, such as ion exchange resins, the present inventors have found that optically active tryptophane of high quality can be recovered in an extremely high yield, in a process of recovering optically active tryptophane from a fermentation liquid or an enzyme reaction mixture which contains large quantities of impurities and liquids obtained at intermediate steps thereof, by firstly performing a filtration using a semi-permeable membrane and then neutralizing the filtrate from the alkaline side under alkaline conditions in the presence of a lower alcohol or a ketone while adding an acid thereto to crystallize the tryptophane. The present invention have thereby accomplished the present invention.

That is, a fermentation liquid or an enzyme reaction mixture or a liquid obtained at an intermediate step thereof is filtered using a semi-permeable membrane. The filtrate is concentrated, if necessary, and a lower alcohol or a ketone is added to the filtrate. In addition, the solution is neutralized for crystallization by reducing pH from an alkaline side while gradually adding an acid such as $H_2SO_4$, HCl, or acetic acid, in an alkaline state maintained using NaOH, $NH_4OH$, etc. As the acid is added, initial crystallization and growth of crystals of tryptophane gradually proceed, whereby glossy $\alpha$-crystals of large hexagonal plates are obtained.

This is asumed to occur because the presence of the lower alcohol or the ketone would relieve an inhibiting action against the initial crystallization and growth of $\alpha$-crystals due to impurities in the progress of the initial crystallization and growth of crystals of tryptophane by neutralization for crystallization from an alkaline side.

To the contrary, when an aqueous solution of tryptophane is neutralized for crystallization from an acidic side, micro $\alpha$-crystals or $\alpha$-crystals aggregate wherein impurities such as coloring materials contaminate the crystals.

For example, tryptophane crystals, obtained when the filtrate (filtered using a semi-permeable membrane) is concentrated for crystallization or neutralized for crystallization in a conventional manner, become aggregated particulate crystals composed of micro crystals which are colored brown and contain large amounts of impurities; when the thus-obtained crystals are dissolved in water, the solution becomes turbid due to the impurities.

On the other hand, tryptophane crystals obtained by performing centrifugal separation using no semi-permeable membrane, concentrating the supernatant under an alkaline condition, and neutralizing the concentrate for crystallization in the presence of a lower alcohol or a ketone, have high purity and minimized coloration and turbidity as compared to the case in which crystallization is conducted from the same solution in a conventional manner (Japanese Patent Application 149752/82).

When filtration using a semi-permeable membrane is used in combination with neutralization for crystallization from an alkaline side in the presence of a lower alcohol or a ketone, it is observed that properties in crystallization are further markedly improved. That is, capability of crystal growth is improved and supersaturation is smoothly released so that contamination of micro crystals initiated by excessive supersaturation is minimized and thick, large crystals of a hexagonal plate shape having uniform graininess can be obtained. As the result, the rate of crystallization is improved. Particularly, separation capability of crystals is improved. For this reason, the purity of tryptophane crystals is extremely good, and materials causing coloration and turbidity can easily remain selectively in the mother liquor.

This phenomenon is believed to be a synergestic effect achieved by filtration using a semi-permeable membrane in combination with crystallization of tryptophane in which the filtrate is neutralized for crystallization from the alkaline side in the presence of a lower alcohol or a ketone. Impurities derived from fermentation liquids, etc., contain large quantities of dissolved proteins, pigments, side products, decomposition products, etc. It is assumed that among these impurities, materials for inhibiting crystallization would be removed by the semi-permeable membrane, whereby α-crystals would stably grow at a subsequent step of neutralization for crystallization without formation of micro crystals due to excessive supersaturation or without crystallization of β-crystals, etc., and a marked effect would result.

The term "fermentation liquid" or "enzyme reaction mixture" referred to in the present invention indicates a broth of L-tryptophane obtained by fermentation using a microorganism or a reaction mixture of L- and D-tryptophane obtained by reaction using an enzyme or a microorganism. The term "liquids obtained at intermediate steps" refers to solutions containing tryptophane obtained at steps prior to the step in which optically active tryptophane is separated and obtained from the fermentation liquid or the enzyme reaction mixture. Examples of such liquids include a bacteria-free solution, a solution after filtration treatment, a mother liquor of crude crystals, a solution of crude crystals, and a solution after treatment with ion exchange resins.

The semi-permeable membrane may be any material for ordinary semi-permeable membranes used in ultrafiltration and reverse osmotic filtration. Examples of semipermeable membranes include polyamide, polyacrylonitrile, cellulose acetate, polysulfone, and polybenzimidazole types. As a shape of the membrane, mention may be made of a tube shape, a flat membrane, a spiral, a hollow thread shape, etc. As a molecular weight for fractionation, approximately 500 to 100,000 may be sufficient, and a fractionating function having a range of 500 to 20,000 is particularly effective.

Various conditions for performing filtration using a semi-permeable membrane may vary within a range specified depending upon each membrane to be used. It should be particularly noted that the filtration is preferably performed at temperatures lower than 60° C. to approximately ambient temperature because there is a tendency that coloration of a treated solution is intensified when the filtration is performed at high temperatures over a long period of time. Further when a large amount of tryptophane remains in the residual liquid after the filtration, the yield decreases; in this case, the concentrated residual liquid after the filtration is diluted with water followed by repeating the filtration.

Means for concentrating the filtrate are not particularly limited. For example, concentration by heating under reduced pressure, concentration by freezing, reverse osmotic concentration, or a combination thereof may be used. In this case, the pH may be varied within a range suitable for each means for concentration. In case that an obstacle occurs due to crystallization of tryptophane at about the isoelectric point (pH 5.9), the filtrate is converted to an acidic or alkaline solution followed by concentration.

As alkalis used for making an alkaline solution of tryptophane, any of NaOH, KOH, LiOH, NH$_4$OH, etc., may be used, and the content is sufficient if the alkali dissolves tryptophane.

The lower alcohols which are to be previously added to raw liquids to be crystallized are those having 1 to 4 carbon atoms, specific examples of which include i-propanol, n-propanol, ethanol, n-butanol, and methanol. As the ketones, acetone and the like may be mentioned. When these lower alcohols or ketones are incorporated in an amount of 5%(v/v) or more, a marked effect can be obtained, but about 10 to 30% is practical.

Optically active tryptophane usually takes either α- or β-crystal form. The α-crystals are in a plate or scale shape, whereas the α-crystals are in a needle form of micro crystals. Accordingly, the crystallization of the α-crystals provides better separation capability and a minimized amount of adhereing mother liquor so that crystals of high quality can be obtained. Tryptophane takes the α-crystals at temperatures higher than a certain temperature (transition point) and the β-crystals at temperatures lower than that. The transition point of tryptophane is approximately 60° C. (aqueous system) but varies depending upon the crystallization system. An accurate transition point at a certain crystallization system can be easily determined by examining crystals which are obtained by subjecting each liquid for crystallization to ordinary crystallization by microscopic observation, powder x-ray diffraction analysis, etc. When an organic solvent is added to the system, the transition point is lowered so that the α-crystals can be obtained stably at lower temperatures as compared to the aqueous system, and the purity and recovery rate of the crystals can be enhanced.

The temperature for crystallization is higher than the transition point as described above. When the temperature range is set forth in a range higher than the transition point, however, neutralization for crystallization followed by a concentration treatment and/or a cooling treatment may be performed for the purpose of controlling the rate of the crystallization. Further, seed crystals may also be used, of course. Furthermore, the β-crystals may not always be crystallized immediately after the crystallization of the α-crystals even though raw liquids for crystallization containing the α-crystals are cooled to temperatures somewhat lower than the transition point; in this case, accordingly, the cooling is discontinued prior to the formation of the β-crystals, and the liquids are subjected to solid-liquid separation, whereby the rate of crystallization increases sometimes. The present invention also includes such an embodiment.

To separate the crystallized crystals, no particular condition is set forth but known methods apply.

Hereafter the present invention will be described more in detail with reference to the examples.

COMPARISON EXAMPLE 1

To a fermentation liquid containing L-tryptophane (Japanese Published Unexamined Patent Application 92796/81) 35% HCl was added until the pH became 3, which was followed by centrifugation. To 10 l of a bacteria-free solution, a 30% NaOH solution was added until the pH became 12.5 and then concentrated. By adding acetic acid to 1600 g (tryptophane content, 10.6%) of the concentrate, neutralization for crystallization was conducted at 45° C. for 2 hours until the pH became 5.9. The system was cooled to 25° C. followed by centrifugation. On the resulting crystals, 500 ml of water was sprinkled to wash the crystals. The crystals were dried at 70° C. under reduced pressure to obtain 148 g of L-tryptophane crystals. Purity, 90.6%; yield, 79.2%; state of solution (transmittance), 10%; filtration with a 0.3μ millipore provided 43% (conditions for measurement of the transmittance: C=1, water, 430 nm).

COMPARISON EXAMPLE 2

To 1 liter of a bacteria-free solution obtained in Comparison Example 1, a 30% NaOH solution was added until the pH became 12.5, and then concentrated. To 133 g (tryptophane content, 12.7%) of the concentrate, 30 ml of isopropyl alcohol was added. Then neutralization for crystallization was carried out at 45° C. for 2 hours until the pH became 5.9, while adding 35% HCl thereto. The system was cooled to 25° C. followed by centrifugation. Onto the resulting crystals a small quantity of water was sprayed to wash the crystals. The crystals were dried at 70° C. under reduced pressure to obtain 15.6 g of L-tryptophane crystals. Purity, 93.4%; yield 86.3%; transmittance, 31%; filtration with a 0.3μ millipore provided 74% (measured under the same conditions as in Comparison Example 1).

COMPARISON EXAMPLE 3

10 liters of a bacteria-free solution obtained in Comparison Example 1 was filtered at 35° C. under a pressure of 2 kg/cm² using a ultrafiltration module ACL-1010 (fractional molecular weight, 13,000) made by Asahi Chemical Industry Co., Ltd. When about 9 l of the filtrate was obtained, 6 l of water was added to the residual liquid after the filtration to dilute, and the thus diluted liquid was filtered to obtain total 15.7 l of the filtrate.

To 2 l of the filtrate, a 30% NaOH solution was added until the pH became 12.5, and the filtrate was concentrated. By adding acetic acid to 202 g (tryptophane content, 10.4%) of the concentrate, neutralization for crystallization was carried out at 45° C. for 2 hours until the pH became 5.9. The system was cooled to 25° C. followed by centrifugation. To the resulting crystals a small quantity of water was sprayed to wash the crystals. The crystals were dried at 70° C. under reduced pressure to obtain 18.1 g of L-tryptophane crystals. Purity, 93.7%; yield 80.8%; transmittance, 34%; filtration with a 0.3μ millipore provided 62% (measured under the same conditions as in Comparison Example 1).

EXAMPLE 1

To 2 l of a ultrafiltrate obtained in Comparison Example 3, a 30% NaOH solution was added until pH became 12.5 and then the filtrate was concentrated. To 155 g (tryptophane content, 13.2%) of the concentrate, 40 ml of isopropyl alcohol was added. Then, neutralization for crystallization was conducted at 45° C. for 2 hours until the pH became 5.9 while adding 35% HCL thereto. The system was cooled to 25° C. followed by centrifugation. To the resulting crystals a small quantity of water was sprayed to wash the crystals. The crystals were dried at 70° C. under reduced pressure to obtain 19.2 g of L-tryptophane crystals. Purity, 98.7%; yield 92.6%; transmittance, 86% (measured under the same conditions as in Comparison Example 1).

COMPARISON EXAMPLE 4

In 4.5 l of water 50 g of L-tryptophane crude crystals obtained in Comparison Example 1 was dissolved. The solution was filtered at 35° C. under a pressure of 20 kg/cm² using a reverse osmotic tubular module PBIL, TL-215 (RO Minitester, N-III Model) made by Teijin Limited. When about 4 l of the filtrate was obtained, 2.5 l of water was added to the residual liquid after the filtration to dilute, and the thus-diluted liquid was filtered to obtain total 6.4 l of the filtrate.

To 3 l of the filtrate, a 30% NaOH solution was added until the pH became 12.5, and then the filtrate was concentrated. By adding acetic acid to 186 g (tryptophane content, 11.0%) of the concentrate, neutralization for crystallization was carried out at 45° C. for 2 hours until the pH became 5.9 with acetic acid. The system was cooled to 25° C. followed by centrifugation. To the resulting crystals a small quantity of water was sprayed to wash the crystals. The crystals were dried at 70° C. under reduced pressure to obtain 17.2 g of L-tryptophane crystals. Purity 98.4%; yield, 82.8%; transmittance, 62%; filtration with a 0.3μ millipore provided 71% (measured under the same conditions as in Comparison Example 1).

EXAMPLE 2

To 3 l of a reverse-osmotic filtrate obtained in Comparison Example 4, a 30% NaOH solution was added until the pH became 12.5, and then the filtrate was concentrated. To 166 g (tryptophane content, 12.4%) of the concentrate, 50 ml of isopropyl alcohol was added. Thereafter, by adding 35% HCl to the mixture, neutralization for crystallization was carried out at 45° C. for 2 hours until the pH became 9.5. The system was cooled to 25° C. followed by centrifugation. To the resulting crystals a small quantity of water was sprayed to wash the crystals. The crystals were dried at 70° C. under reduced pressure to obtain 18.6 g of L-tryptophane crystals. Purity, 99.3%; yield, 88.5%; transmittance, 97% (measured under the same conditions as in Comparison Example 1).

What is claimed is:

1. A method for the recovery of optically active tryptophane, which comprises:
    filtering a solution of optically active tryptophane containing impurities through a semipermeable membrane;
    adding a lower alcohol or acetone to the filtrate;
    maintaining said solution containing said lower alcohol or acetone at an alkaline pH by the addition of alkaline hydroxide and at a temperature higher than the α/β crystalline transition point;
    adding acid to said solution, thereby causing α-crystals of optically active, substantially pure L or D-tryptophane to form in said solution; and
    separating said crystals from said solution containing impurities.

2. The method of claim 1 wherein said semipermeable membrane has a fractionating function in the range of from approximately 500 to 100,000.

3. The method of claim 1 wherein the filtration is conducted at a temperature lower than 60° C.

4. The method of claim 1 wherein said solution is maintained alkaline with NaOH, KOH, LiOH, or NH₄OH.

5. The method of claim 1 wherein said lower alcohol is i-propanol, n-propanol, ethanol, n-butanol, or methanol.

6. The method of claim 1 wherein said ketone is acetone.

7. The method of claim 1 wherein said lower alcohol or ketone is incorporated in an amount of at least 5% (v/v).

8. The method of claim 7 wherein said amount is from about 10 to 30%.

9. The method of claim 1 wherein said pH is maintained at an alkaline pH of 12.5 prior to adding acid.

10. The method of claim 1 wherein acid is added until the pH becomes 5.9.

* * * * *